United States Patent
Paik et al.

(10) Patent No.: US 10,342,755 B2
(45) Date of Patent: Jul. 9, 2019

(54) COSMETIC COMPOSITION COMPRISING SPECIFIC COMBINATION OF SURFACTANTS

(71) Applicant: AMOREPACIFIC CORPORATION, Seoul (KR)

(72) Inventors: Byung Ryol Paik, Yongin-si (KR); Byung Young Kang, Yongin-si (KR); Soon Ae An, Yongin-si (KR); Joon Young Hwang, Yongin-si (KR); Wha Young Shin, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 5 days.

(21) Appl. No.: 15/563,114

(22) PCT Filed: Sep. 7, 2015

(86) PCT No.: PCT/KR2015/009410
§ 371 (c)(1),
(2) Date: Sep. 29, 2017

(87) PCT Pub. No.: WO2016/159457
PCT Pub. Date: Oct. 6, 2016

(65) Prior Publication Data
US 2018/0071202 A1    Mar. 15, 2018

(30) Foreign Application Priority Data

Mar. 31, 2015 (KR) .................. 10-2015-0045696

(51) Int. Cl.
| | |
|---|---|
| A61K 8/06 | (2006.01) |
| A61K 8/92 | (2006.01) |
| A61Q 19/00 | (2006.01) |
| A61K 8/60 | (2006.01) |
| A61K 8/04 | (2006.01) |
| A61K 8/31 | (2006.01) |
| A61K 8/37 | (2006.01) |
| A61K 8/58 | (2006.01) |
| A61K 8/891 | (2006.01) |
| A61Q 5/00 | (2006.01) |
| A61Q 17/04 | (2006.01) |

(52) U.S. Cl.
CPC ............. *A61K 8/922* (2013.01); *A61K 8/042* (2013.01); *A61K 8/062* (2013.01); *A61K 8/31* (2013.01); *A61K 8/37* (2013.01); *A61K 8/585* (2013.01); *A61K 8/60* (2013.01); *A61K 8/602* (2013.01); *A61K 8/604* (2013.01); *A61K 8/608* (2013.01); *A61K 8/891* (2013.01); *A61Q 19/00* (2013.01); *A61Q 19/007* (2013.01); *A61K 2800/262* (2013.01); *A61K 2800/412* (2013.01); *A61Q 5/00* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 2008/0267897 A1 | 10/2008 | Giroud et al. | |
| 2014/0230841 A1 | 8/2014 | Mathonneau | |

FOREIGN PATENT DOCUMENTS

| | | |
|---|---|---|
| KR | 10-1998-0055066 | 10/1998 |
| KR | 10-2004-0094506 | 11/2004 |
| KR | 10-2008-0085301 | 9/2008 |
| KR | 10-2009-0056321 | 6/2009 |

OTHER PUBLICATIONS

International Search Report for PCT/KR2015/009410 dated Dec. 29, 2015, 2 pages.
Written Opinion of the ISA for PCT/KR2015/009410 dated Dec. 29, 2015, 6 pages.

*Primary Examiner* — Kevin S Orwig
(74) *Attorney, Agent, or Firm* — Nixon & Vanderhye P.C.

(57) ABSTRACT

The present invention relates to a cosmetic composition, in which a high-content of oil-soluble components is stabilized using a natural surfactant, and more specifically to a cosmetic composition, in which by using a plant-derived natural surfactant and a high-pressure emulsification method without using PEG-based or ionic surfactants that may cause skin irritation, a transparent gel formulation containing a high-content of oil-soluble components can be realized, thereby effectively combining the advantage of an oil formulation excellent in moisturizing power, and the advantages of a moisture gel formulation, which is easy to use without flowing down, and has a fresh feeling of use.

17 Claims, No Drawings

COSMETIC COMPOSITION COMPRISING SPECIFIC COMBINATION OF SURFACTANTS

This application is the U.S. national phase of International Application No. PCT/KR2015/009410 filed 7 Sep. 2015, which designated the U.S. and claims priority to KR Patent Application No. 10-2015-0045696 filed 31 Mar. 2015, the entire contents of each of which are hereby incorporated by reference.

TECHNICAL FIELD

The present invention relates to a cosmetic composition in which a high-content of oil-soluble components is stabilized by using a natural surfactant, and more specifically to a cosmetic composition in which, by using a plant-derived natural surfactant and a high-pressure emulsification method without using PEG-based or ionic surfactants that may cause skin irritation, a transparent gel formulation containing a high-content of oil-soluble components can be realized, thereby effectively combining the advantages of an oil formulation excellent in moisturizing power and gloss property, and the advantages of a moisture gel formulation, which is easy to use without flowing down, and has a fresh feeling of use.

BACKGROUND ART

Oil formulations supply nutrients to the skin and provide gloss and moisturizing power to the skin, but they lack fresh moisturizing content and are inconvenient to use because they flow down when drawn off into a hand and applied to the face due to low viscosity. In recent years, to overcome these inconveniences of customers, extensive studies have been conducted on oil-in-water type (O/W) emulsions containing moisturizing content by stabilizing high contents of oil-soluble components by manufacturers.

The easiest stabilization of the high contents of oil-soluble components is to increase the viscosity of water phase using a carbopol-based or acryl-based thickening agent together with a surfactant. However, an O/W emulsion manufactured by these methods is not distinguished from a conventional lotion or cream formulation in terms of formulation, and also there is a problem that it is difficult to exhibit inherent feelings of use and properties of the oil-soluble components.

For these reasons, it is the latest trend that the manufacturers are studying methods for manufacturing a transparent gel in which a high content of oil-soluble components stabilized by making the oil-soluble components into small particles in a size of 200 nm or less by using a high-pressure emulsification method. The gel thus manufactured has a transparency and high viscosity as the particles of the oil-soluble components are small, and little or no thickening agent can be used. Thus, when it is applied, it exhibits a formulation similar to a moisture gel in the initial stage, and when it is rolled on the skin, the gel structure is easily collapsed to give a high moisture content, but at the end, it not only leaves a film of oil-soluble components on the skin, but also allows the soluble components.

In order to make small particles of 200 nm or less using such a high-pressure emulsification method and to manufacture a transparent gel, is common to make the particle size of the oil-soluble components small together with a polyglyceryl-based surfactant or to use a polyethylene-based (PEG) surfactant or an ionic surfactant for stabilizing an interface film together. However, when the PEG-based surfactant or ionic surfactant is used, there is a safety concern that it causes skin irritation. Nevertheless, the reason for using a PEG-based surfactant or an ionic surfactant in general because it is difficult to reduce the particle size of a nano-emulsion containing a high-content of oil-soluble components or to stabilize an interface film if the use of these surfactants is excluded. Thus, it would be difficult to realize the transparency characteristic of the solubilized gel formulation, and to guarantee the product quality for a long time in various environments (low temperature, high temperature, etc.) in which customers use the product.

PRIOR ART DOCUMENT (Patent Document 1) Korean Application Publication No. 2008-0085301

DISCLOSURE

Technical Problem

Therefore, in order to reflect recent awareness of the customers on the increased skin safety, the present inventors have attempted to implement the advantages of the high content of oil-soluble components, which are made into small particles by a high-pressure emulsification method, in terms of feeling of use that they rapidly convert or change from gel to oil without the help of the PEG-based surfactant and ionic surfactant, and to find out a method of stabilizing the same in a transparent gel state by using only a plant-derived emulsifier in order to allow the customers to feel the inherent feeling of the oil-soluble components.

As such, it is one object of the present invention to stabilize the high content of oil-soluble components having a small particle size in the form of a transparent gel only with a plant-derived emulsifier, without the PEG-based surfactant and ionic surfactant that cause strong s in irritation, thereby providing a cosmetic composition which combines the advantages of a gel-type composition and an oil-type composition in terms of stability and feeling of use of the formulation.

Technical Solution

In order to achieve the object above, the present invention provides a cosmetic composition comprising a plant-derived surfactant; and an oil-soluble component.

Advantageous Effects

The composition of the present invention can provide a skin-friendly composition by using a combination of plant-derived surfactants, without using a PEG-based surfactant and an ionic surfactant that cause skin irritation, and it can simultaneously provide the advantages of an oil formulation excellent in moisturizing power and gloss property, and the advantages of a moisture gel formulation, which is easy to use without flowing down and has a transparency and a fresh feeling of use, by containing a high content or oil-soluble components granulated to a size of 200 nm or less, which provides a feeling of use that changes from gel to oil.

DETAILED DESCRIPTION OF THE EMBODIMENTS

The present invention relates to a cosmetic composition comprising a mixture of plant-derived surfactants, and oil-soluble components. In particular, the cosmetic composition of the present invention is the form of a transparent gel, and is preferably an oil-in-water type (O/W) composition. In addition, the composition of the present invention is characterized by providing a feeling of use that changes from gel to oil upon application to the skin.

In particular, the cosmetic composition according to the present invention excludes the use of a PEG-based surfactant and an ionic surfactant, and can secure a long-term stability while providing excellent skin safety by using a plant-derived surfactant.

As used herein, the term "oil-soluble component" refers to a substance that does not dissolve in water but dissolves in oil, solvent or the like.

The cosmetic composition of the present invention contains oil-soluble components in a high content, in particular, in an amount of 10 to 60% by weight based on the total weight of the composition, thereby providing not only moisture content but also moisturizing power and gloss property, which are inherent properties of the oil-soluble components. If the oil-soluble components are contained in an amount of less than 10% by weight, it is not possible to provide moisturizing power and gloss property of the oil-soluble components and to implement the shape-retaining properties of a gel due to low viscosity. If the amount is more than 60% by weight, it is difficult to ensure a long-term stability of the formulation, and the feeling of use of the composition is reduced because the moisture content of the composition is reduced.

The cosmetic composition of the present, invention is preferably formulated into an oil-in-water type, in particular, into a transparent gel with a viscosity of 3,000 cps or higher, so as to provide a fresh feeling of use while containing oil-soluble components. This because if the viscosity is less than 3,000 cps, it is difficult to experience the feeling of use that changes due to a collapse of the gel structure. In addition, if there is no transparency, it cannot be recognized as a composition such as a moisture gel, making it difficult to distinguish it from a common emulsion of O/W formulation.

The composition of the present invention employs a high-pressure emulsification method as one means for stabilizing the oil-soluble components, and by this method, the oil-soluble particles are made into small particles having a particle size of 200 nm or less and are incorporated into the composition. If the particles are formed with a particle size exceeding 200 nm, not only the transparency of the formulation is lost, but also the particle size increases over time, or the fusion between the particles of the oil-soluble components occurs, thereby failing to secure a long-term stability.

In addition, the present invention uses a plant-derived surfactant to stabilize the particles of oil-soluble components, which are made into a size of 200 nm or less by using a high-pressure emulsification method as described above. As a plant-derived surfactant, at least one selected from the group consisting of alkyl glucoside-based surfactant and methyl glucoside sesquistearate; and polyglyceryl-based surfactant are mixed and used. The polyglyceryl-based surfactant used in the present invention can effectively pack the interface film due to a large hydrophilic portion, and the alkyl glucoside-based surfactant has a high HLB value ranging from 9 to 19, thereby effectively reducing the particle size. In addition, the methylglucose sesquistearate used in the present invention is a mixture of methyl glucoside, monoester and diester of stearic acid, and can effectively stabilize oil particles. Instead of using only one type of polyglyceryl-based surfactant, by using other types of surfactants in combination as described above, the oil-soluble particles can be made smaller and stabilized for a long period of time.

In the present invention, as a polyglyceryl-based surfactant, at least one selected from the group consisting of polyglyceryl-3 methylglucose distearate, polyglyceryl-2 stearate, polyglyceryl-10 stearate and the like may be used, but is not limited thereto.

In the present invention, as an alkyl glucoside-based surfactant, at least one selected from the group consisting of cetearyl glucoside, decyl glucoside, coco-glucoside, $C_{12-20}$ alkyl glucoside, $C_{10-16}$ alkyl glucoside, and the like may be used, but is not limited thereto.

The composition of the present invention preferably uses, as a plant-derived surfactant, a polyglyceryl-based surfactant by mixing with at least one selected from the group consisting of alkyl glucoside-based surfactant and methylglucose sesquistearate, more preferably with two or more thereof. Most preferably, a mixture of polyglyceryl-3 methylglucose distearate, methylglucose sesquistearate and cetearyl glucoside may be used.

The cosmetic composition of the present invention contains the plant-derived surfactant in an amount of 0.10 to 0.20 parts by weight based on 1 part by weight of the oil-soluble components. If the ratio of the plant-derived surfactant to the oil-soluble component is less than 0.1, the particles of oil-soluble components of 200 nm or less are not formed, and thus the composition may be suspended or cannot be distinguished from a common emulsion in terms of feeling of use due to low viscosity. If the ratio exceeds 0.20, the content of the surfactant is high, which increases hardness, thereby exhibiting cream-like properties, and the feeling of use is masked due to a hard texture, and thus it is not preferable to obtain desired physical properties of a formulation. In addition, preferably, the present invention uses at least one of alkyl glucoside-based surfactant or methylglucose sesquistearate by mixing at a ratio of 0.01 to 0.40 parts by weight, preferably 0.01 to 0.34 parts by weight based on 1 part by weight of the polyglyceryl-based surfactant. More preferably, the present invention uses alkyl glucoside by mixing at a ratio of 0.01 to 0.17 parts by weight, and methylglucose sesquistearate by mixing at a ratio of 0.01 to 0.17 parts by weight based on 1 part by weight of the polyglyceryl-based surfactant. Most preferably, methylglucose sesquistearate is used by mixing at a ratio of 0.01 to 0.17 parts by weight, and cetearyl glucoside is used by mixing at a ratio of 0.01 to 0.17 parts by weight based on 1 part by weight of the polyglyceryl-based surfactant.

Examples of the oil-soluble components used in the present invention include at least one selected from a solid-phase component including fats, waxes, higher alcohols, higher fatty acids, hydrocarbons and the like, which have a melting point of 30° C. or higher and are solid at room temperature; or a liquid phase component including oils, esters, ethers, hydrocarbons, and the like. Specifically, examples of the solid-phase components include fat including shea butter, mango seed butter and cacao seed butter, etc.; wax including myristyl myristate, camellia sinensis leaf extract, jojoba, sunflower seed, carnauba wax, candelilla wax and beeswax, etc.; higher alcohol including cetyl alcohol, stearyl alcohol and behenyl alcohol, etc.; higher fatty acid including caprylic/capric triglyceride, lauric acid, myristic acid, palmitin acid and stearic acid, etc.; hydrocarbon including ceresin, etc. Further, examples of the liquid-phase components include natural oil including meadowfoam seed oil, sunflower seed oil, macadamia seed oil, green tea seed oil, ginger oil, ginseng oil, coconut oil, olive oil and camellia oil, etc.; ester including phytosteryl/octyldodecyl lauroyl glutamate, isostearyl isostearate, methylheptyl isostearate, dicaprylyl carbonate and isopropyl palmitate, etc.; ether including dicaprylyl ether, etc.; silicone oils including dimethicone, cyclopentasiloxane, cyclohexasiloxane, phenyltrimethicone, trisiloxane and methyltrimethicone, etc.; and hydrocarbon including squalane, etc.

In addition, the cosmetic composition according to the present invention may contain an appropriate amount of auxiliary components such as polyol, ethanol, extract, functional efficacy component, coloring agent, flavoring agent, thickening agent, preservative, and the like conventionally used in the manufacture of an oil-in-water cosmetic composition, and preferably, they may be contained in an amount of 0 to 90% by weight based on the total weight of the cosmetic composition.

The cosmetic composition according to the present invention can be widely applied, without particular limitation in the formulation thereof, as skin care cosmetic compositions including cosmetic water, essence, lotion, cream, UV-blocking agent; hair cosmetic compositions, such as hair tonic including hair essence or hair treatment; and other medicines and quasi-drugs, etc.

DETAILED DESCRIPTION OF THE EMBODIMENTS

Hereinafter, the present invention will be described in more detail by way of Examples and Experimental Examples. However, these Examples are given for illustrative purposes only, and the scope of the invention is not intended to be limited by these Examples. Modifications, substitutions and additions conventionally known in the art are intended to include within the scope of the present invention.

[Reference Example] Preparation of Example and Comparative Examples

Oil-in-water emulsions of Example 1 and Comparative Examples 1 to 6 were each prepared by a conventional manufacturing method by using the composition shown in the following Table 1 (unit: wt %) in accordance with the following manufacturing method. Herein, in Comparative Example 1, the content of the oil-soluble components was contained in an amount less than 10%, which is less than the appropriate range. In Comparative Example 2, the total amount of the plant-derived surfactant was contained in a less amount of less than 0.10 parts by weight compared to the content of the oil-soluble components. In Comparative Example 3, no other surfactants were included in the mixture of the plant-derived surfactants besides the polyglyceryl-based surfactant. In Comparative Example 4, a polyglyceryl-based surfactant was not included in the mixture of the plant-derived surfactants. In Comparative Example 5, the total amount of the mixture of the plant-derived surfactants was used in excess of 0.20 parts by weight compared to the content of the oil-soluble components. In Comparative Example 6, the content of the polyglyceryl-based surfactant in the mixture of the plant-derived surfactants was used in excess of the ratio of 0.01 to 0.17 parts by weight of methylglucose sesquistearate and 0.01 to 0.17 part by weight of cetearyl glucoside based on 1 part by weight of the polyglyceryl-based surfactant. The plant-derived surfactants used herein, that is, polyglyceryl-3 methylglucose distearate, methylglucose sesquistearate and cetearyl glucoside were all obtained from Morechem Co., Ltd (Seoul, Korea).

TABLE 1

| Number | Name of Component | Example 1 | Comparative Example 1 | Comparative Example 2 | Comparative Example 3 | Comparative Example 4 | Comparative Example 5 | Comparative Example 6 |
|---|---|---|---|---|---|---|---|---|
| 1 | Purified water | To 100 | To 100 | To 100 | To 100 | To 100 | To 100 | To 100 |
| 2 | polyglyceryl-3 methylglucose distearate | 5.00 | 1.16 | 2.00 | 5.00 | 0.00 | 10.00 | 0.50 |
| 3 | methylglucose sesquistearate | 0.67 | 0.15 | 0.27 | 0.00 | 2.68 | 1.34 | 2.68 |
| 4 | cetearyl glucoside | 0.50 | 0.12 | 0.20 | 0.00 | 2.00 | 1.00 | 2.00 |
| 5 | Olive oil | 7.90 | 1.80 | 7.90 | 7.90 | 7.90 | 7.90 | 7.90 |
| 6 | Cyclopentasiloxane* Cyclohexasiloxane | 7.90 | 1.78 | 7.90 | 7.90 | 7.90 | 7.90 | 7.90 |
| 7 | A mixture of hydrocarbon-based oil, ester-based oil, natural oil, and silicone-based oil | 24.1 | 5.44 | 24.1 | 24.1 | 24.1 | 24.1 | 24.1 |
| 8 | Preservatives | 0.20 | 0.20 | 0.20 | 0.20 | 0.20 | 0.20 | 0.20 |
| 9 | Ethylhexylglycerin | 0.05 | 0.05 | 0.05 | 0.05 | 0.05 | 0.05 | 0.05 |
| 10 | Polyol | 8.10 | 8.10 | 8.10 | 8.10 | 8.10 | 8.10 | 8.10 |
| 11 | Ethanol | 5.00 | 5.00 | 5.00 | 5.00 | 5.00 | 5.00 | 5.00 |
| 12 | Flavoring agent | 0.17 | 0.17 | 0.17 | 0.17 | 0.17 | 0.17 | 0.17 |

<Preparation Method>

1) Oil-in-water type emulsions were prepared using raw materials 1 to 12 shown in Table 1 above.

2) Emulsions were deaerated and then applied with a pressure of 3 Cycle or higher at 1,000 bar using M-110EH-30 Microfluidizer® Processor (Microfluidics Co., Ltd) to prepare a final cosmetic composition.

[Experimental Example 1] Evaluation of Physical Properties According to the Content of the Oil-Soluble Components and the Combination Ratio of the Surfactants The physical properties the oil-in-water type emulsions of Example 1 and Comparative Examples 1 to 6 were evaluated with respect to viscosity, particle size of the oil-soluble components and transparency of the compositions. The viscosity was measured using a Brookfield Viscometer LVDV-II (Spindle No. 4, 12 rpm). In addition, the particle size was measured using a Malvern Zen 3600 Zetasizer. The results of the viscosity and particle size measurements are shown in Table 2 below.

TABLE 2

|  | Viscosity(cps) | Particle Size(nm) | Transparency and appearance |
|---|---|---|---|
| Example 1 | 21,000 | 149.9 | Transparent gel |
| Comparative Example 1 | 50 | 141.8 | Suspended liquid |
| Comparative Example 2 | 3,990 | 209.8 | White emulsion |
| Comparative Example 3 | 15,097 | 170.7 | Suspended gel |
| Comparative Example 4 | 21,445 | 136.9 | Transparent gel |
| Comparative Example 5 | Viscosity measurement not possible due to cream-phase having high hardness | 547.9 | White cream |
| Comparative Example 6 | 23,395 | 135.1 | Transparent gel | sion was formed and thus the transparency was not exhibited. In Comparative Example 5, the composition was formulated into a cream phase having a very high hardness of the composition because a high content of the plant-derived surfactants was used, and thus it did not provide a desired feeling of use.

In contrast, Example 1 according to the present invention was found to have desired physical properties by being formulated into a transparent gel form.

[Experimental Example 2] Evaluation of Stability According to the Content of the Oil-Soluble Components and the Combination Ratio of the Surfactants The stability of the oil-in-water type emulsions of Example 1 and Comparative Examples 1 to 6 was evaluated by the degree of separation of the composition over time.

The oil-in-water type emulsions of Example 1 and Comparative Examples 1 to 6 were stored for 4 weeks in a thermostat at −10° C., 5° C., 30° C., 37° C., 45° C. and 60° C., and the stability of the compositions was observed weekly. At this time, the samples stored at −10° C. were thawed at room temperature every week to observe the stability, and then were stored back in a freezer. The results of observation are shown in Table 3 below.

TABLE 3

| | Temperature | | | | | |
|---|---|---|---|---|---|---|
| | −10° C. | 5° C. | 30° C. | 37° C. | 45° C. | 60° C. |
| Example 1 | Stable | Stable | Stable | Stable | Stable | Stable |
| Comparative Example 1 | Stable | Stable | Stable | Degree of suspension increased | Degree of suspension increased | Degree of suspension increased |
| Comparative Example 2 | Stable | Stable | Stable | Degree of suspension increased | Degree of suspension increased | Degree of suspension increased |
| Comparative Example 3 | Stable | Stable | Stable | Stable | Stable | Stable |
| Comparative Example 4 | Viscosity reduced | Stable | Stable | Stable | Stable | Stable |
| Comparative Example 5 | — | — | — | — | — | — |
| Comparative Example 6 | Viscosity reduced | Stable | Stable | Stable | Stable | Stable |

* Note:
In Comparative Example 5, oil oozing occurred during the manufacturing process and the stability was not observed As can be confirmed from Table 2, Comparative Example 1 could not implement a gel-type formulation due to a low content of the oil-soluble components, and the emulsion was formulated into a suspended liquid which did not provide transparency. In Comparative Example 2, the particle size of the oil-soluble components exceeded 200 nm, and it was difficult to distinguish the feeling of use from a common emulsion. Further, in Comparative Example 3, since the surfactants, other than the polyglyceryl-based surfactant, were not included, the composition in the form or suspen- As can be confirmed from Table 3, in Comparative Examples 1 and 2, the degree of suspension increased at a high temperature. In Comparative Examples 4 and 6, the viscosity was reduced at a temperature below zero. In Comparative Example 5, a phenomenon, in which the oil-soluble components oozed out on the surface, was observed, and thus the formulation stability was not good.

In contrast, it was confirmed in Example 1 according to the present invention that the stability of the formulation was maintained regardless of the storage temperatures.

[Experimental Example 3] Evaluation of Feeling of Use According to the Content of the Oil-Soluble Components and the Combination Ratio of the Surfactants The feeling of use on oil-in-water type emulsions of Example 1 and Comparative Examples 1 to 6 was evaluated after application to the skin.

Example 1 exhibited a feeling of use according to a rapid change of state from gel to oil, whereas in Comparative Example 1, there was no experience on the feeling of use according to a change of state from gel to oil, because the liquid had almost no viscosity due to a low content of the oil-soluble components. In Comparative Example 2, the viscosity was low so that there was a lack of feeling use according to the change of state from gel to oil, and the feeling of use was not distinguishable from a common emulsion. Comparative Examples 3, and 6 exhibited a feeling of use according to a rapid change of state from gel to oil similar to that of the composition according to the present invention, and thus were suitable in terms of feeling of use. In Comparative Example 5, the emulsion was hard exhibiting a property like cream having a high hardness and thus was not able to spread out.

The invention claimed is:

1. A cosmetic emulsion composition comprising a plant-derived surfactant; and an oil-soluble component,
    wherein the plant-derived surfactant is a mixture of an alkyl glucoside-based surfactant, methyl glucoside sesquistearate and a polyglyceryl-based surfactant,
    wherein the plant-derived surfactant is used in an amount of 0.10 to 0.20 parts by weight based on 1 part by weight of the oil-soluble component,
    wherein the alkyl glucoside-based surfactant and methyl glucose sesquistearate are each mixed at a ratio of 0.01 to 0.17 parts by weight based on 1 part by weight of the polyglyceryl-based surfactant, and
    wherein the oil-soluble component is present in the form of particles having a size of 200 nm or less, and contained in an amount of 10 to 60% by weight based on the total weight of the composition.

2. The cosmetic emulsion composition of claim 1, wherein the polyglyceryl-based surfactant is at least one selected from the group consisting of polyglyceryl-3 methyl glucose distearate, polyglyceryl-2 stearate and polyglyceryl-10 stearate.

3. The cosmetic emulsion composition of claim 1, wherein the alkyl glucoside-based surfactant is at least one selected from the group consisting of cetearyl glucoside, decyl glucoside, coco-glucoside, $C_{12-20}$ alkyl glucoside and $C_{10-16}$ alkyl glucoside.

4. The cosmetic emulsion composition of claim 1, wherein the oil-soluble component is at least one selected from the group consisting of fats, waxes, higher alcohols, higher fatty acids, hydrocarbons, natural oils, esters, ethers, silicone oils, and mixtures thereof.

5. The cosmetic emulsion composition of claim 1, wherein the composition is an oil-in-water emulsion.

6. The cosmetic emulsion composition of claim 1, wherein the composition has a viscosity of 3,000 cps or higher.

7. The cosmetic emulsion composition of claim 1, wherein the composition is in the form of a transparent gel.

8. The cosmetic emulsion composition of 1, wherein the composition undergoes a phase change from gel to oil upon application to the skin.

9. The cosmetic emulsion composition of claim 4, wherein the oil-soluble component comprises at least one fat selected from the group consisting of shea butter, mango seed butter, and cacao seed butter.

10. The cosmetic emulsion composition of claim 4, wherein the oil-soluble component comprises at least one wax selected from the group consisting of myristyl myristate, camellia sinensis leaf extract, jojoba, sunflower seed, carnauba wax, candelilla wax, and beeswax.

11. The cosmetic emulsion composition of claim 4, wherein the oil-soluble component comprises at least one higher alcohol selected from the group consisting of cetyl alcohol, stearyl alcohol, and behenyl alcohol.

12. The cosmetic emulsion composition of claim 4, wherein the oil-soluble component comprises at least one higher fatty acid selected from the group consisting of caprylic/capric triglyceride, lauric acid, myristic acid, palmitic acid, and stearic acid.

13. The cosmetic emulsion composition of claim 4, wherein the oil-soluble component comprises at least one natural oil selected from the group consisting of meadowfoam seed oil, sunflower seed oil, macadamia seed oil, green tea seed oil, ginger oil, ginseng oil, coconut oil, olive oil, and camellia oil.

14. The cosmetic emulsion composition of claim 4, wherein the oil-soluble component comprises at least one ester selected from the group consisting of phytosteryl/octyldodecyl lauroyl glutamate, isostearyl isostearate, methylheptyl isostearate, dicaprylyl carbonate, and isopropyl palmitate.

15. The cosmetic emulsion composition of claim 4, wherein the oil-soluble component is dicaprylyl ether.

16. The cosmetic emulsion composition of claim 4, wherein the oil-soluble component comprises at least one silicone oil selected from the group consisting of dimethicone, cyclopentasiloxane, cyclohexasiloxane, phenyltrimethicone, trisiloxane, and methyltrimethicone.

17. The cosmetic emulsion composition of claim 4, wherein the oil-soluble component comprises at least one hydrocarbon selected from the group consisting of ceresin and squalane.

* * * * *

UNITED STATES PATENT AND TRADEMARK OFFICE
CERTIFICATE OF CORRECTION

| | |
|---|---|
| PATENT NO. | : 10,342,755 B2 |
| APPLICATION NO. | : 15/563114 |
| DATED | : July 9, 2019 |
| INVENTOR(S) | : Paik et al. |

Page 1 of 1

It is certified that error appears in the above-identified patent and that said Letters Patent is hereby corrected as shown below:

In the Specification

Column 1, Line 60, is replaced with:
-- but also allows the user to experience the inherent feeling of use of the oil-soluble components. --

Column 2, Line 37, is replaced with:
-- and ionic surfactant that cause strong skin irritation, thereby --

Column 2, Line 59, is replaced with:
-- feeling of use, by containing a high content of oil-soluble --

Column 4, Line 65, is replaced with:
-- myristic acid, palmitic acid and stearic acid, etc.; hydrocar- --

Column 9, Line 18, is replaced with:
-- emulsion. Comparative Examples 3, 4 and 6 exhibited a --

Signed and Sealed this
Twenty-second Day of October, 2019

Andrei Iancu
*Director of the United States Patent and Trademark Office*